United States Patent [19]

Davis et al.

[11] Patent Number: 4,624,835

[45] Date of Patent: Nov. 25, 1986

[54] MICROCENTRIFUGATION TUBE FOR THE CONCENTRATION OF SAMPLES FOR ELECTRON MICROSCOPY

[75] Inventors: Charles P. Davis; Robert Outenreath, both of Galveston, Tex.

[73] Assignee: Board of Regents, The University of Texas System, Austin, Tex.

[21] Appl. No.: 682,573

[22] Filed: Dec. 14, 1984

Related U.S. Application Data

[63] Continuation of Ser. No. 414,630, Sep. 3, 1982, abandoned.

[51] Int. Cl.[4] .......... B01L 3/14; B04B 7/10; C12M 1/24; G01N 1/06

[52] U.S. Cl. .......... 422/102; 356/246; 422/72; 435/296; 494/16

[58] Field of Search .......... 422/72, 102; 356/246; 494/16, 17; 435/296

[56] References Cited

U.S. PATENT DOCUMENTS

| | | | |
|---|---|---|---|
| 2,817,970 | 12/1957 | Whitby | 73/61.4 |
| 3,363,503 | 1/1968 | Shifrin | 356/246 |
| 3,475,127 | 10/1969 | Gilford | 73/863.21 X |
| 3,738,811 | 6/1973 | Cheng | 436/93 X |
| 3,814,522 | 6/1974 | Clark et al. | 422/102 X |
| 4,066,414 | 1/1978 | Selby | 422/102 |
| 4,094,641 | 6/1978 | Friswell | 422/102 X |
| 4,105,415 | 8/1978 | Lovett | 356/246 X |
| 4,106,907 | 8/1978 | Charlton et al. | 422/72 X |
| 4,162,896 | 7/1979 | Hosli | 422/102 X |
| 4,512,202 | 4/1985 | Wright et al. | 422/102 X |

OTHER PUBLICATIONS

Polysciences, Inc. 1982/83, *Microtomy and Embedding Aids*, p. 162.

Specimen Preparation Embedding Supplies, Fullam, 1980.

*Primary Examiner*—David L. Lacey
*Assistant Examiner*—Robert J. Hill, Jr.
*Attorney, Agent, or Firm*—Arnold, White & Durkee

[57] ABSTRACT

A microcentrifugation tube for the preparation of a sample for examination under an electron microscope is disclosed. The tube has a bore extending from the top of the tube to the base of the tube. The bore includes an upper section comprising inner walls which taper conically inwardly toward the base of the tube at an included angle of less than 25° and a lower tip extending from the lower end of the upper section to the base of the tube, wherein the lower tip has a cross-sectional shape sized to accommodate the slicing of such a sample on a microtome when removed from the tube.

4 Claims, 8 Drawing Figures

MICROCENTRIFUGATION TUBE FOR THE CONCENTRATION OF SAMPLES FOR ELECTRON MICROSCOPY

This application is a continuation of application Ser. No. 414,630, filed Sept. 3, 1982 now abandoned.

BACKGROUND OF THE INVENTION

The invention relates to the preparation of samples for viewing with an electron microscope and, more particularly, it relates to a microcentrifugation tube for the concentration of samples of cells for examination under an electron microscope.

A continual problem encountered by many investigators in in scientific research is the obtaining of adequate samples for experimentation and subsequent processing for electron microscopy. This is especially true for those investigators who work with cell cultures, bacteria cultures, and viral samples. It is a special problem where experimental samples are obtained in individual lots from human volunteers wherein the quantity of the sample is often limited and the obtaining of multiple samples is often difficult or impossible.

The adequacy of the sample size is critical because of the number of steps through which a sample must go during the preparation of the sample for examination by an electron microscope. In particular, the processing of a sample may include fifteen to twenty steps, each of which entails centrifuging the sample to separate and remove unwanted matter. Unfortunately, each of these steps may result in a significant loss of sample cell population to the point wherein the sample is essentially lost.

Specifically, the preparation of a sample may include the steps of first removing a sample of cells from the human subject and centrifuging the cells to collect them. A protein fixative is then added to cross-link the proteins, following which the sample is rinsed twice to remove any of the unreacted protein fixative. Of course, each of these rinses involves the use of the centrifuge to remove the rinse and the unreactive fixative. A fixative for the membranes is then added, following which the sample is again rinsed twice to remove any unreacted membrane fixative. The sample is then rinsed with ethanol for as many as seven different concentrations of ethanol in order to remove any water in the sample. A commercial imbedding medium is then added, which is typically a plastic, in two different concentrations, each of which are substantially removed from the sample, again by centrifugation. The sample is then mixed with a final imbedding medium and an accelerator and the sample and imbedding medium are centrifuged to pull the sample cells to the bottom of the mixture. The imbedding medium is then treated (usually by heating) to cause the medium to harden into a hard polymerized plastic which is the final sample product.

This final plastic product is then sliced on a microtome in sections having a thickness on the order of 500 to 900 Å for viewing under an electron microscope.

It should be emphasized that because of the centrifugation of the sample following each of the steps the potential for loss of part of the sample cell population in each step is significant. Accordingly, if the beginning sample cell population is small, the sample may be essentially lost before the procedure is through. Indeed, it has been the experience of the present inventors that for some samples, the preparation of the sample so diminished the sample cell population that the resulting product was essentially worthless for meaningful examination.

A contributing cause to the loss of cell population during processing is the tube currently available and most commonly used to prepare the final sample. Specifically, the tube currently used has a bottom cross-sectional area which is too large to be suitable for the slicing of the sample on the microtome. From this lower cross-sectional area, the inner walls of the tube flair at an included angle of approximately 45° for a given distance at which the walls proceed upwardly parallel to each other. It has been found that for the angle of approximately 45°, the sample cells tend to gather along the walls of the tube instead of migrating to the bottom of the tube as desired. Accordingly, the opportunity for the loss of sample cell population at each step is magnified by the number of cells which adhere to the gently sloping sides.

The migration of cells to the sloping side is disadvantageous for yet another reason. In particular, since the capsules presently available have a lower cross-sectional area which is too large for slicing in the microtome, the final sample product must be trimmed at the bottom in order to allow the insertion of the sample into the microtome for slicing. Accordingly, those cells which have migrated and adhered to the gently sloping sides will almost invariably be trimmed from the sample in the final preparation of the sample for slicing in the microtome.

The capsule presently available therefore enhances the loss of cells during each early preparatory step of the sample and almost invariably insures the loss of some cells during the trimming of the sample for slicing on the microtome.

It is therefore desirable to provide a tube which both minimizes the congregation of cells along its sides and prevents the loss of cells by trimming for slicing in the microtome.

SUMMARY OF THE INVENTION

Accordingly, the present invention provides a microcentrifugation tube for the preparation of samples for examination under an electron microscope which includes a bore extending from the top of the tube to the base of the tube. The bore includes an upper section comprising inner walls which taper conically inwardly toward the base of the tube at an included angle of less than 25° and a lower tip extending from the lower end of the upper section to the base of the tube wherein the lower tip has a cross-sectional shape sized and adapted to accomodate the slicing of such a sample on a microtome when the sample is removed from the tube.

It will be understood that since the tube will typically be destroyed upon removal from the sample at the end of the preparation of the sample, the outer shape of the tube is not critical. The only restraints on the outer shape and material of the tube are that they accomodate the removal of the tube from the sample without destroying the sample and that they be adaptable to the centrifuge for efficient centrifugation of the sample. In one aspect of the preferred embodiment, the exterior of the tube includes a longitudinal score along its length which is adapted to accomodate the removal of the tube from the sample. In another embodiment of the present invention, the exterior of the tube has a latitudinal score around its perimeter adapted to facilitate the removal of the tube from the sample.

In an alternative embodiment of the present invention, the bore may include a gripping section extending upwardly from the top of the above-mentioned upper section, wherein the gripping section has at least two parallel walls spaced at a preselected width suitable for clamping between a pair of jaws on a microtome for slicing.

Accordingly, the present invention overcomes the previous discussed problems by providing a microcentrifugation tube having steeply slanted sides which minimize the congregation of cells along them. The preferred embodiment further includes a sample tip adapted in dimension for the insertion and slicing of the sample in a microtome.

BRIEF DESCRIPTION OF THE DRAWINGS

This invention will further be illustrated by reference to the appended drawings which illustrate particular embodiments of the microcentrifugation tube in accordance with this invention.

DESCRIPTION OF THE PREFERRED EMBODIMENTS

The preferred embodiment is generally represented by a microcentrifugation tube having a bore extending from the top of the tube to the base of the tube wherein the lower section of the bore tapers inwardly toward the base of the tube at a preselected included angle. While it is believed that the included angle should not exceed approximately 25° in order to minimize cell concentration along the sides, the included angle of the preferred embodiment of the present invention is substantially 10°. As will be explained in greater detail below, the tube of the preferred embodiment will also include a tip especially shaped and adapted for slicing in a microtome. It is believed, however, that the steeper walls of the present invention enhance cell concentration at the bottom of the tube and thereby increase the viability of experimentation with samples of smaller cell concentration, with or without the specially shaped tip.

Figure 1:
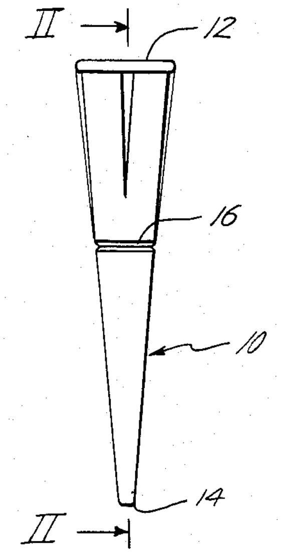
FIG. 1 is a side view of a microcentrifugation tube in accordance with the present invention.
Figure 2:
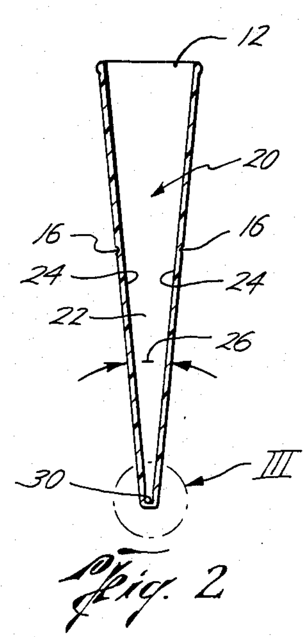
FIG. 2 is a sectional view taken along section line II—II in FIG. 1.

Referring now to FIGS. 1 and 2 the preferred embodiment is represented by a tube 10 having a top 12 and a base 14. The tube 10 has a generally conical outer shape converging from the top 12 to the base 14. The conical shape of the tube 10 is truncated at the base 14 such that the tube 10 essentially forms the frustum of a cone.

The exterior of the tube 10 further includes a latitudinal score 16 extending around the perimeter of the tube 10 at a preselected distance from the top of the tube. The scoring 16 extends inwardly into the surface of the tube to a suitable depth to accomodate the separation of the tube 10 during the removal of the tube 10 from a completed sample.

Referring again to FIG. 2, the tube 10 has a longitudinal bore 20 extending from the top 12 of the tube 10 to the base 14. The bore includes an upper section 22 comprising inner walls 24 which taper conically inwardly toward the base of the tube at an included angle 26.

In the preferred embodiment, the included angle is substantially 10°. It will be understood, however, that the included angle may vary slightly so long as the sides are steep enough to prevent the collection of cells along the inner walls 24 during centrifugation of the cell sample. In this regard, it is believed that the included angle should not exceed 25° to adequately minimize the collection of cells along the tube walls.

Figure 3:
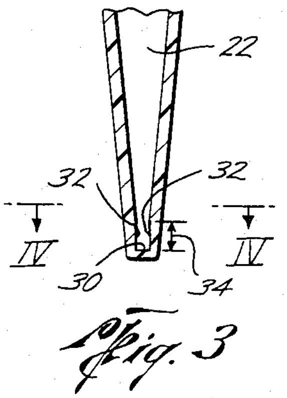
FIG. 3 is an exploded view illustrating the tip of the tube shown in FIG. 2.
Figure 4:
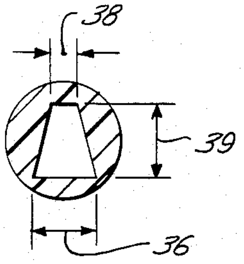
FIG. 4 is a sectional view taken along section line IV—IV in FIG. 3, illustrating the cross section of the preferred embodiment of the tube at its tip.

Referring still to FIG. 2, the bore 20 of the preferred embodiment further includes a lower tip section 30 extending from the lower end of the upper section 22 to the base 14 of the tube 10. The lower tip 30 has a horizontal cross-sectional shape adapted to accommodate the slicing of the final sample product on a microtome when the sample product is removed from the tube 10. Referring to FIGS. 3 and 4 the tip section 30 includes inner walls 32 which are configured to be substantially vertical in use. That is, the walls 32 do not converge or taper, but rather maintain a constant horizontal cross-sectional relationship to each other such that the horizontal cross-sectional shape and area of the lower tip section 30 remains substantially constant along its length.

Referring now to FIG. 4, in the preferred embodiment, the lower tip 32 has a generally trapezoidal configuration and horizontal cross-section. It has been found that the use of the trapezoidal configuration provides a sample tip yielding the least distortion upon slicing by the microtome. It will be understood, however, that other horizontal cross-sectional shapes suitable for minimizing the distortion of the sample upon slicing in the microtome may be utilized in accordance with the invention.

Similarly, it will be understood that the particular dimensions of the tip section 30 may vary depending upon the particular microtome application for which the tube is desired. In the preferred embodiment, the tip 30 has a length 34 of approximately 1 millimeter. The widths of the bases 36 and 38 of the trapezoidal horizontal cross-section are approximately 0.25 millimeters and 0.12 millimeters respectively and the height 39 of the trapezoidal horizontal cross-section is approximately 0.5 millimeters.

Figure 5:
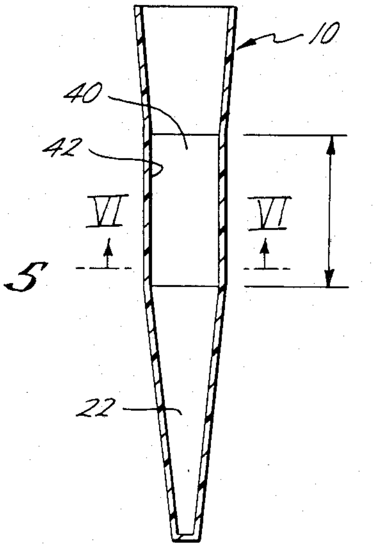
FIG. 5 is a sectional view of an alternative embodiment of FIG. 1 having a section of parallel sides for gripping in the microtome.
Figure 6:
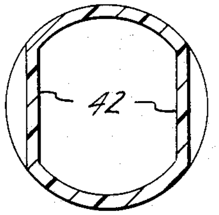
FIG. 6 is a sectional view of the microcentrifugation tube shown in FIG. 5 taken along the lines VI—VI.

In an alternative embodiment of the present invention, the bore of the tube 10 may further be modified to provide a gripping section for a set of clamp jaws for a given microtome. Referring now to FIG. 5, there is shown a tube 10 further including a gripping section 40 extending upwardly from the top of the upper section 22. As shown in FIG. 6, the gripping section 40 includes at least two parallel inner walls 42 spaced at a preselected width suitable for insertion between a given pair of jaws on a microtome.

Figure 7:
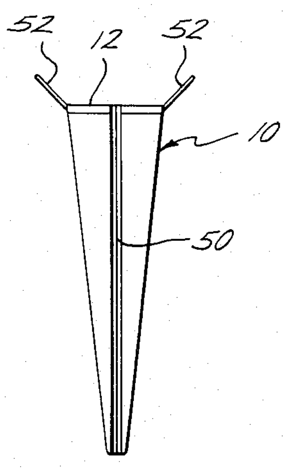
FIG. 7 is a side view of an alternative embodiment of the tube shown in FIG. 1.
Figure 8:
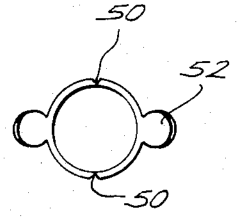
FIG. 8 is a plan view of the tube shown in FIG. 7.

Referring now to FIG. 7, there is shown another alternative embodiment of the microcentrifugation tube 10 of the present invention. In this embodiment, the tube 10 includes a longitudinal score 50 (as opposed to the latitudinal score 16 shown in FIGS. 1 and 2). The tube 10 may further include a plurality of tabs 52 attached near the top 12 of the tube 10 and adapted to accommodate the removal of the tube 10 from a completed sample.

Hence, the present invention provides a tube which has an inner shape adapted to minimize the collection of cells from a sample along its sides upon centrifugation. The inner shape of the tube is also adapted to provide a finished polymerized plastic sample adapted for slicing in a microtome without further modification of the sample. It is the inventor's experience and belief that the present invention makes possible the utilization of cell samples having 10 to 100 times fewer cells than had previously been possible.

The instant invention has been disclosed in connection with specific embodiments. However it will be apparent to those skilled in the art that variations for the illustrated embodiments may be undertaken without departing from the spirit and scope of the invention. For example, the horizontal cross-sectional configuration of the tip 30 could be modified to a number of polygonal or irregular shapes providing adequate stability for slicing on the microtome. Further, the walls 32 of the tip 30 could also be tapered at the included angle so long as the horizontal cross-sectional area of the tip is adapted and sized to be suitable for slicing on the microtome. These and other variations will be apparent to those skilled in the art and are within the spirit and scope of the present invention.

What is claimed is:

1. A microcentrifugation tube comprising a tube having an exterior surface, an open upper end, a closed lower end, and means defining a bore extending from the open upper end of the tube to the closed lower end of the tube, said means defining a bore including a lower tip and an upper section, said lower tip extending upwardly from the closed lower end of the tube about 1 millimeter and having a substantially constant trapezoidal horizontal cross-sectional shape that has a height of approximately 0.5 millimeters and bases of approximately 0.25 millimeters and approximately 0.12 millimeters, said upper section comprising inner walls which taper conically inwardly to said lower tip at an included angle of substantially 10°, and wherein the sizes and shapes of the lower tip and upper section are such that a cell population of a sample placed in said tube may be concentrated and the sample embedded in plastic to provide a finished polymeric plastic sample that is removable from the tube and has a shape to facilitate slicing the plastic sample with a microtome and minimize distortion of the plastic sample during slicing to thereby prepare the sample for examination under an electron microscope.

2. The tube of claim 1 wherein the exterior surface of the tube has a longitudinal score along its length adapted to accommodate removal of the tube from a sample.

3. The tube of claim 1 wherein the exterior surface of the tube has a latitudinal score around its perimeter adapted to accommodate removal of the tube from a sample.

4. The tube of claim 1 wherein the means defining a bore also includes a top section extending upwardly from said upper section, the top section having at least two parallel interior walls spaced at a preselected width.

* * * * *